(12) United States Patent
Moharir

(10) Patent No.: US 12,691,157 B2
(45) Date of Patent: Jul. 28, 2026

(54) METHOD FOR REMOVING ANTINUTRIENT FROM TURMERIC SPICE

(71) Applicant: NUTRITIONAL CONSULTANTS UNLIMITED, INC., Mesa, AZ (US)

(72) Inventor: Yadunath Moharir, Mesa, AZ (US)

(73) Assignee: NUTRITIONAL CONSULTANTS UNLIMITED, INC., Mesa, AZ (US)

( * ) Notice: Subject to any disclaimer, the term of this patent is extended or adjusted under 35 U.S.C. 154(b) by 621 days.

(21) Appl. No.: 17/985,876

(22) Filed: Nov. 13, 2022

(65) Prior Publication Data

US 2023/0158097 A1 May 25, 2023

Related U.S. Application Data

(60) Provisional application No. 63/403,298, filed on Sep. 2, 2022.

(51) Int. Cl.
| | |
|---|---|
| *A61K 36/9066* | (2006.01) |
| *A23L 5/20* | (2016.01) |
| *A23L 27/10* | (2016.01) |
| *A23L 33/105* | (2016.01) |
| *A61K 9/14* | (2006.01) |
| *B01D 11/02* | (2006.01) |

(52) U.S. Cl.
CPC ............ *A61K 36/9066* (2013.01); *A23L 5/23* (2016.08); *A23L 27/11* (2016.08); *A23L 33/105* (2016.08); *A61K 9/14* (2013.01); *B01D 11/0288* (2013.01); *A61K 2236/331* (2013.01); *A61K 2236/39* (2013.01); *A61K 2236/51* (2013.01); *A61K 2236/53* (2013.01)

(58) Field of Classification Search
CPC .. A61K 2236/53; A61K 36/9066; A61K 9/14; A61K 2236/331; A61K 2236/39; A61K 2236/51; B01D 11/0257; B01D 11/0284; B01D 11/0288; A23L 27/14; A23L 5/23; A23L 27/11; A23L 33/105; A23V 2002/00; A23V 2250/2112
See application file for complete search history.

(56) References Cited

U.S. PATENT DOCUMENTS

| | | | |
|---|---|---|---|
| 3,340,250 | A | 9/1967 | Sair |
| 6,224,877 | B1 | 5/2001 | Gaikar |
| 7,736,679 | B2 | 6/2010 | Antony |
| 8,568,802 | B2 | 10/2013 | Gokaraju |
| 10,231,940 | B2 | 3/2019 | Pather |
| 10,231,992 | B2 | 3/2019 | Castro Feo |
| 2005/0244522 | A1 | 11/2005 | Carrara |
| 2010/0098789 | A1 | 4/2010 | Balambika |
| 2011/0184146 | A1 | 7/2011 | Srinivas |
| 2012/0003177 | A1 | 1/2012 | Shen |
| 2012/0177758 | A1 | 7/2012 | Minami |
| 2019/0060253 | A1 | 2/2019 | Antony |
| 2019/0200660 | A1 | 7/2019 | Miyamoto |

FOREIGN PATENT DOCUMENTS

| | | |
|---|---|---|
| KR | 1020070079305 A | 8/2008 |

OTHER PUBLICATIONS

Government of Canada, How to Test for Chloride Ions in Iron Treatment Solutions Using Silver Nitrate, 2018, 19 pages. <https://www.canada.ca/en/conservation-institute/services/conservation-preservation-publications/canadian-conservation-institute-notes/test-chloride-ions-iron-treatment-silver-nitrate>. (Year: 2018).*

Clark, J., Testing for negative ions, 2020, Chemguide: Core Chemistry 14-16, 5 pages. <https://www.chemguide.co.uk/14to16/analysis/anions.html>. (Year: 2020).*

Starling, S., Turmeric is safe, says Sabinsa, 2017, NutraIngredients USA, 6 pages. <https://www.nutraingredients-usa.com/Article/2009/02/27/Turmeric-is-safe-says-Sabinsa/>. (Year: 2017).*

PowderProcess, Moisture content of powders, 2020, 5 pages. <https://web.archive.org/web/20200928022120/https://powderprocess.net/Powder_Flow/Moisture_Content.html>. (Year: 2020).*

MIT OpenCourseWare, Extraction and Washing Guide, 2012, Chemistry Laboratory Techniques, 4 pages. <https://ocw.mit.edu/courses/5-301-chemistry-laboratory-techniques-january-iap-2012/a0317f969aa17d5eb5aa9064d9c08df8_MIT5_301IAP12Work_Handout.pdf>. (Year: 2012).*

Pawar, H.A., et al., A Novel and Simple Approach for Extraction and Isolation of Curcuminoids from Turmeric Rhizomes, 2018, Nat Prod Chem Res, 6:1, 4 pages. <DOI: 10.4172/2329-6836.1000300>. (Year: 2018).*

(Continued)

*Primary Examiner* — Aaron J Kosar
*Assistant Examiner* — Jennifer Lynn Cain
(74) *Attorney, Agent, or Firm* — COOPER LEGAL GROUP LLC

(57) ABSTRACT

The present invention provides a method for removing antinutrients from turmeric spice. The antinutrient such as oxalic acid is removed by using the method of present invention and thus the toxicity associated with it is also eliminated. The method includes preparing the turmeric powder and repetitively extracting the turmeric powder with inorganic acid. The turmeric powder is stirred in a pre-defined volume and pre-determined concentration of the inorganic acid for pre-defined time with constant agitation at pre-determined temperature to obtain a turmeric paste. The turmeric paste is then washed with water and dried to obtain the purified turmeric powder.

8 Claims, 2 Drawing Sheets

(56)  References Cited

OTHER PUBLICATIONS

Liu, Y., et al., Extraction and Determination of Total and Soluble Oxalate in Pulping and Papermaking Raw Materials, 2015, BioResources, 10(3):4580-4587, 9 pages. <DOI: 10.15376/biores.10.3.4580-4587>. (Year: 2015).*

U.S. Appl. No. 10/989,874, filed Nov. 15, 2004, Guan Jie Chen.

U.S. Appl. No. 16/171,117, filed Oct. 25, 2018, Benny Antony.

U.S. Appl. No. 11/725,140, filed Mar. 16, 2007, Robert T. Gow.

U.S. Appl. No. 12/514,009, filed Nov. 8, 2007, Mohsen Daneshtalab.

U.S. Appl. No. 17/266,324, filed Aug. 5, 2019, Pascale Elizabeth Renée Fanca.

U.S. Appl. No. 12/479,894, filed Jun. 8, 2009, David B. Tuchinsky.

U.S. Appl. No. 16/274,623, filed Feb. 13, 2019, Andrea Giori.

U.S. Appl. No. 14/652,492, filed Aug. 19, 2014, Sreeraj Gopi.

U.S. Appl. No. 12/343,750, filed Dec. 24, 2008, Thomas M. DiMauro.

U.S. Appl. No. 13/360,005, filed Jan. 27, 2012, Krishnakumar Illathu Madhavam.

U.S. Appl. No. 12/460,474, filed Jul. 20, 2009, Kailash Chandra Agarwal.

U.S. Appl. No. 17/348,911, filed Jun. 16, 2021, Jermy.

U.S. Appl. No. 11/016,773, filed Dec. 21, 2004, Bin Kikuchi.

U.S. Appl. No. 09/616,417, filed Jul. 14, 2000, Seiri Oshiro.

U.S. Appl. No. 13/497,992, filed Sep. 21, 2010, Toshiya Minami.

* cited by examiner

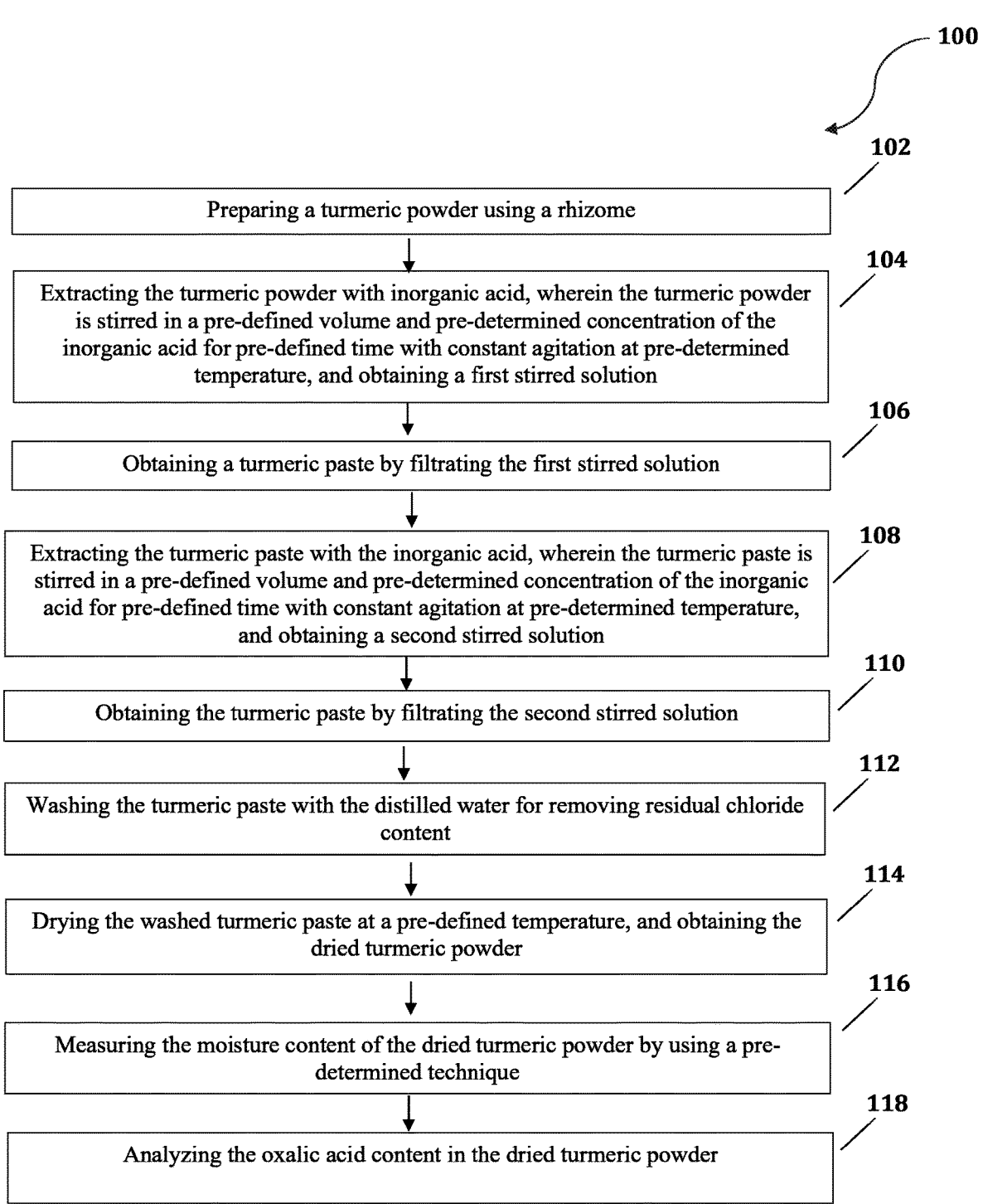

100

102

Preparing a turmeric powder using a rhizome

104

Extracting the turmeric powder with inorganic acid, wherein the turmeric powder is stirred in a pre-defined volume and pre-determined concentration of the inorganic acid for pre-defined time with constant agitation at pre-determined temperature, and obtaining a first stirred solution

106

Obtaining a turmeric paste by filtrating the first stirred solution

108

Extracting the turmeric paste with the inorganic acid, wherein the turmeric paste is stirred in a pre-defined volume and pre-determined concentration of the inorganic acid for pre-defined time with constant agitation at pre-determined temperature, and obtaining a second stirred solution

110

Obtaining the turmeric paste by filtrating the second stirred solution

112

Washing the turmeric paste with the distilled water for removing residual chloride content

114

Drying the washed turmeric paste at a pre-defined temperature, and obtaining the dried turmeric powder

116

Measuring the moisture content of the dried turmeric powder by using a pre-determined technique

118

Analyzing the oxalic acid content in the dried turmeric powder

Figure 1

METHOD FOR REMOVING ANTINUTRIENT FROM TURMERIC SPICE

CROSS-REFERENCE TO RELATED APPLICATION

This application claims the benefit of U.S. Provisional Application No. 63/403,298 filed 2 Sep. 2022, which is incorporated herein by reference in its entirety.

TECHNICAL FIELD

The present invention relates generally to a method for removing antinutrient from spices. More specifically, the present invention relates to a method for removing antinutrient from turmeric spice.

BACKGROUND

Turmeric is a plant of ginger family. Turmeric is obtained from the rhizome of *Curcuma longa linn.* (curcuma domestic valeton) belonging to the natural order Zingiberaceae. Turmeric is also known as Curcuma, Curcumin, Halada, Haldi, Haridra, Indian Saffron, Nisha, Pian Jiang Huang, Rajani, Safran Bourbon, Safran de Batallita, Safran des Indes, Turmeric Root, and Yu Jin.

Turmeric powder contains about 60-70% carbohydrates, 6-13% water, 6-8% protein, 5-10% fat, 3-7% dietary minerals, 3-7% essential oils, 2-7% dietary fiber, and 1-6% curcuminoids. Curcuminoids, include mainly curcumin (de-ferulolylmethane), demethoxycurcumin and bis demethoxycurcumin. Curcumin is responsible for providing yellow color to the turmeric.

Turmeric is widely used as culinary spices and also a traditional medicine for treating disorders of the skin, upper respiratory tract, joints, and digestive system. In present age, it is promoted as a dietary supplement for a variety of conditions, including arthritis, digestive disorders, respiratory infections, allergies, liver disease, depression, and many others.

Turmeric is proving to be beneficial in the treatment of many health conditions including Alzheimer's disease, and it also useful because of its Analgesic activity, Anti-bacterial activity, Anti-cancerous activity, Anti-coagulant property, Antioxidant activity, Cardio protective activity, Gastrointestinal track protective activity, Healing property, Hepatoprotective activity, skin care treatment, treating respiratory diseases, and treating rheumatoid arthritis.

In contrast with the numerous medicinal uses of turmeric, it has been shown to contain high level of antinutrient, such as, oxalate, free oxalic acid, tannins, phenols, flavonoids, alkaloids, saponins and other antinutrients, which are harmful to human being.

The oxalate is a salt or ester of oxalic acid. It exists in two different forms in plant foods, as free oxalic acid, salts with sodium, potassium and ammonium ions, and insoluble salts with calcium, magnesium and iron ions. The insoluble oxalates form the insoluble salts in the digestive track by binding with the cations such as calcium and magnesium, which are excreted from the human body. As the essential minerals get removed, there is decrease in the bioavailability of these essential minerals. However, the soluble oxalate has to be excreted in the urine, in this process of excretion, the oxalate forms the insoluble calcium oxalate by binding with the calcium, which then accumulated in the kidney and ultimately increases the risk of kidney stones and other associated health problems.

Considering the increased use of turmeric in recent years, the need for providing a pure and antinutrient free turmeric has become crucial study for researchers.

In order to reduce the effect of the antinutrients in the spices and at the same time retaining as much as macro and micronutrients, various techniques have been used. The traditional methods used for purifying the spices includes processing the spices, boiling of the spices up to boiling point, and thereafter, spreading out under the sun for drying or shade drying.

However, these traditional methods do not prove to eliminate the antinutrients in most effective quantity and there are also chances of degradation of various macro and micronutrients or essential component from the spices.

Therefore, there is a need of optimizing a best method for removal of the antinutrients from the spices without hampering the essential nutrients of the product.

SUMMARY

Embodiments of the present invention present technological improvements as solutions to one or more of the above-mentioned technical problems.

This summary is provided to introduce aspects related to antinutrient free turmeric. This summary is not intended to identify essential features of the claimed invention nor it is intended for use in determining or limiting the scope of the present invention.

The present invention relating to method for removing antinutrient from turmeric spice, it is to be understood that this application is not limited to the particular system(s) and methodologies described, as there can be multiple possible embodiments which are not expressly illustrated in the present invention. It is also to be understood that the terminology used in the description is for the purpose of describing the implementations or versions or embodiments only and is not intended to limit the scope of the present invention.

In one of the embodiments, the present invention discloses a method for removing antinutrients from turmeric spice, which includes a step of preparing a turmeric powder using a rhizome. The method includes a step of extracting the turmeric powder with inorganic acid. In this, the turmeric powder is stirred in a pre-defined volume and pre-determined concentration of the inorganic acid for pre-defined time with constant agitation at pre-determined temperature, and obtaining a first stirred solution. Thereafter, a turmeric paste is obtained by filtrating the first stirred solution. This turmeric paste is then extracted using the inorganic acid, wherein the turmeric paste is stirred in a pre-defined volume and pre-determined concentration of the inorganic acid for pre-defined time with constant agitation at pre-determined temperature which provides a second stirred solution then the turmeric paste has been obtained by filtrating the second stirred solution. The turmeric paste is then washed with the distilled water for removing residual chloride content. The obtained turmeric paste is then subjected to drying at a pre-defined temperature range to obtain the dried turmeric powder. The moisture content of the dried turmeric powder is measured by using a pre-determined technique, wherein the moisture content is below a threshold value. In a final method step, the oxalic acid content of the dried turmeric powder is analyzed.

In another embodiments, a purified turmeric powder comprising active nutrient components has a total content of oxalic acid below 100 ppm.

Additional aspects, advantages, features and objects of the present invention would be made apparent from the drawings and the detailed description of the illustrative embodiments. It will be appreciated that features of the present invention are susceptible to being combined in various combinations without departing from the scope of the present invention as defined by the below mentioned detailed description and drawings.

BRIEF DESCRIPTION OF ACCOMPANYING DRAWINGS

The detailed description is described with reference to the accompanying figures.

FIG. 1 illustrates a flow chart depicting a method for removing antinutrient from turmeric spice with repetitive extraction, in accordance with an exemplary implementation of the present invention.

Figure 2:
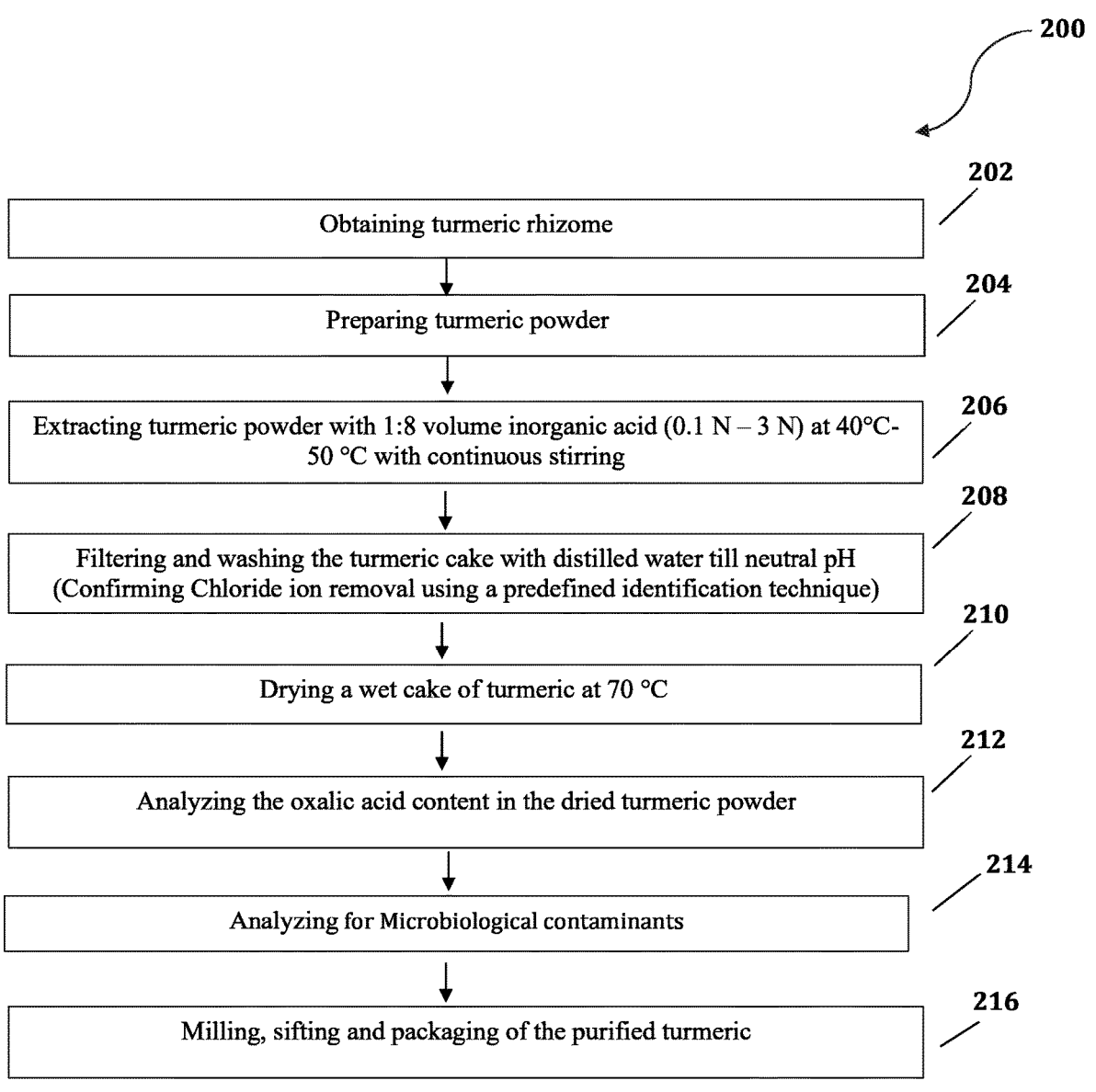
FIG. 2 illustrates a flow chart depicting a method for removing antinutrient from turmeric spice, in accordance with an embodiment of the present invention.

Further, the figures depict various embodiments of the present subject matter for purposes of illustration only. One skilled in the art will readily recognize from the following discussion that alternative embodiments of the structures and methods illustrated herein may be employed without departing from the principles of the present invention described herein.

DETAILED DESCRIPTION

The invention will now be described with reference to the accompanying embodiments which do not limit the scope and ambit of the invention. The description provided is purely by way of example and illustration.

The embodiments herein and the various features and advantageous details thereof are explained with reference to the non-limiting embodiments in the following description. Descriptions of well-known components and processing techniques are omitted so as to not unnecessarily obscure the embodiments herein. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

The foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the embodiments as described herein.

Some embodiments of this invention, illustrating all its features, will now be discussed in detail. The words "comprising," "having," "containing," and "including," and other forms thereof, are intended to be equivalent in meaning and be open ended in that an item or items following any one of these words is not meant to be an exhaustive listing of such item or items, or meant to be limited to only the listed item or items. It must also be noted that as used herein and in the appended claims, the singular forms "a," "an," and "the" include plural references unless the context clearly dictates otherwise.

In an aspect of the present invention, in order to overcome the above referenced problems and to provide various advantages elaborated in the subsequent section, a method for removing antinutrients is disclosed.

In the following description, for the purpose of explanation, specific details are set forth in order to provide an understanding of the present invention. It will be apparent, however, to one skilled in the art that the present invention may be practiced without these details. One skilled in the art will recognize that embodiments of the present invention, some of which are described below, may be incorporated into a number of systems.

The method for removing antinutrient and preparing a turmeric with minimum toxic effect has been provided in the present invention. Another object of the present invention is to provide a simple and economical process for removal of antinutrients from the spices. The present invention provides an optimized method for the removal of antinutrients and also provides a purified product retaining essential components with minimum adverse effect on consumption.

In one of the embodiments, the present invention discloses a method for removing antinutrients from turmeric spice, which includes a step of preparing a turmeric powder using a rhizome. The method includes a step of extracting the turmeric powder with inorganic acid. In this, the turmeric powder is stirred in a pre-defined volume and pre-determined concentration of the inorganic acid for pre-defined time with constant agitation at pre-determined temperature, and obtaining a first stirred solution. Thereafter, a turmeric paste is obtained by filtrating the first stirred solution. This turmeric paste is then extracted using the inorganic acid, wherein the turmeric paste is stirred in a pre-defined volume and pre-determined concentration of the inorganic acid for pre-defined time with constant agitation at pre-determined temperature which provides a second stirred solution then the turmeric paste has been obtained by filtrating the second stirred solution. The turmeric paste is then washed with the distilled water for removing residual chloride content. The obtained turmeric paste is then subjected to drying at a pre-defined temperature range to obtain the dried turmeric powder. The moisture content of the dried turmeric powder is measured by using a pre-determined technique, wherein the moisture content is below a threshold value. In a final method step, the oxalic acid content of the dried turmeric powder is analyzed.

In another embodiments, a purified turmeric powder comprising active nutrient components has a total content of oxalic acid below 100 ppm.

In another implementation, the rhizomes are ground to make a powder and passed 100% through #100 mesh for obtaining the turmeric powder.

In another implementation, the temperature of distilled water is optimized between room temperature to 50 degrees Celsius (° C.).

In another implementation, the method is optimized for concentration of the inorganic acid in a range from 0.1 Normal (N)-3 Normal (N).

In another implementation the inorganic acid is selected from a group consisting of Hydrochloric acid (HCl) and sulfuric acid (H2SO4).

In another implementation the inorganic acid is Hydrochloric acid (HCl).

In another implementation, the temperature of the method is optimized in between 25° C. to 50° C.

In another implementation, the method is carried out at temperature in a range of 40° C. to 50° C.

In another implementation, the agitation is carried out at temperature in a range of 40° C. to 50° C.

In another implementation, the turmeric paste is dried at a temperature in a range of 50° C. to 70° C.

In another implementation, the extraction is carried out for 2 hours to 3 hours.

In another implementation, a ratio of the turmeric powder to the inorganic acid is 1:8 and 1:4.

In another embodiment, the analysis of oxalic acid content is carried out by using a High-Performance Liquid Chromatography or Gas chromatography-mass spectrometry (GC-MS) technique.

In another implementation, the step of washing the turmeric paste with the distilled water for removing residual chloride content also comprises the steps of, checking a potential of hydrogen ion concentration (pH) value of filtrate obtained after washing the turmeric paste; adding a silver nitrate solution to the filtrate; and observing an appearance of white precipitate or turbidity in the filtrate.

In another implementation, the step of washing the turmeric paste with the distilled water for removing residual chloride content is repeated till obtaining a clear filtrate.

In another implementation, removal of chloride ion is confirmed by addition of Silver Nitrate to the filtrate resulting a white precipitate of Silver Chloride.

In another implementation, a purified turmeric powder includes active nutrient components. In an exemplary embodiment, the total content of oxalic acid is below 100 ppm.

In another embodiment, the analysis of oxalic acid content is carried out using High Performance Liquid Chromatography (HPLC) or Gas chromatography-mass spectrometry (GC-MS) technique.

In another implementation, the step of washing the turmeric paste with the distilled water for removing residual Sulfate ion is confirmed by addition of Barium chloride or Barium Nitrate to the filtrate that gives a white precipitate (turbidity) of Barium Sulfate.

In another implementation, the final product is then undergoing a milling process in order to prepare uniform particle sized turmeric powder.

In another implementation, the final turmeric powder is then shifted to a packaging unit for final packing of pure turmeric powder.

In an embodiment of the present invention, a method to remove antinutrient from turmeric and thus eliminating the toxicity associates with the antinutrient is provided. The method is optimized to determine the best method for elimination or removal of the antinutrient, preferably oxalic acid. The optimized method preserves the active ingredient of the turmeric and thus preserving the beneficial desired benefits of turmeric spice. The optimized method of present invention is economic, simple and highly efficient.

The method of the present invention provides a purified turmeric which can be consumed safely by eliminating risk of health issues linked with the vital organs.

In another implementation, the final turmeric powder after removal the oxalic acid, which is responsible for the formation of kidney stones, can be considered as a safer form of turmeric (Curcuma longa). Consumption of the safer form of turmeric supports maintenance of healthy kidneys and prevents further damage to the kidneys by maintaining a healthy kidney function.

In another implementation, a use of the safer form of turmeric spice in food preparations does not affect the taste of the food that it is added to and/or it's nutritional value as a spice.

In another implementation, a use of safer form of turmeric spice in food preparations, intensifies the yellow coloration imparted to the preparation, in comparison with using regular turmeric spice.

In another implementation, a safer form of turmeric spice can be mixed with other common spices to prepare various spice combinations which are used for preparing different food dishes, by making the secondary products, safer.

FIG. 1 illustrates a flow diagram (100) depicting a method for removing antinutrients with repetitive extraction, in accordance with an implementation of the present invention.

The flow chart starts at a step (102), preparing a turmeric powder using a rhizome. In an embodiment, the turmeric rhizomes are collected and sorted out to use for a next step. In an exemplary embodiment, the turmeric powder is prepared by griding the turmeric rhizome and passing 100% through mesh #100. At a step (104), extracting the turmeric powder with inorganic acid, wherein the turmeric powder is stirred in a pre-defined volume and pre-determined concentration of the inorganic acid for pre-defined time with constant agitation at pre-determined temperature, and obtaining a first stirred solution. At a step (106), obtaining a turmeric paste by filtrating the first stirred solution. In an embodiment, the turmeric powder is extracted with the inorganic acid at predetermined temperature, in pre-defined volume and pre-determined concentration with continuous stirring, and obtaining a first stirred solution. At a step (108), extracting the turmeric paste with the inorganic acid, wherein the turmeric paste is stirred in a pre-defined volume and pre-determined concentration of the inorganic acid for pre-defined time with constant agitation at pre-determined temperature, and obtaining a second stirred solution. At a step (110), obtaining the turmeric paste by filtrating the second stirred solution. In an embodiment, the turmeric paste is again extracted with inorganic acid at predetermined temperature, in pre-defined volume and pre-determined concentration with continuous stirring, and obtains a second stirred solution.

At a next step (112), washing the turmeric paste with the distilled water for removing residual chloride content. In an embodiment, the turmeric paste is washed with the purified water. In one embodiment, the step of washing the turmeric paste with the distilled water for removing residual chloride content is repeated till obtaining a clear filtrate. The pre-defined identification technique is used for confirming the total removal of chloride ion.

At a step (114), drying the washed turmeric paste at a pre-defined temperature range and obtaining the dried turmeric powder. At a step (116), measuring the moisture content of the dried turmeric powder by using a pre-determined technique, wherein the moisture content is below a threshold value. In an embodiment, measuring the moisture content of the dried turmeric powder is carried out by using a pre-determined technique.

At a final step (118), analyzing the oxalic acid content of the dried turmeric powder. In an embodiment, the analysis of oxalic acid content is carried out using, but is not limited to, High Performance Liquid Chromatography (HPLC) or Gas chromatography-mass spectrometry (GC-MS) technique. In an embodiment, the HPLC and GC-MS techniques are well known in art.

FIG. 2 illustrates a flow diagram (200) depicting a method for removing antinutrients, in accordance with an implementation of the present invention.

The flow chart (200) starts at a step (202), obtaining the turmeric rhizome. In an embodiment, the turmeric rhizomes are collected and sorted out to use for next step. At a step (204), preparing turmeric powder, the turmeric powder is prepared by griding the turmeric rhizome and passing 100% through mesh #100. At a step (206), extracting turmeric powder with 1:8 volume inorganic acid at 40° C.-50° C. with continuous stirring. In an embodiment, the turmeric powder is extracted with inorganic acid, with a pre-defined concentration in 1:8 ratio, at 40° C.-50° C., with continuous stirring.

At a step (208), filtering and washing the turmeric cake with distilled water till neutral pH. In an embodiment, the turmeric paste is obtained by filtrating the stirred solution and the wet cake of turmeric paste is washed with the purified water. In one embodiment, the step of washing the turmeric paste with the distilled water for removing residual chloride content is repeated till obtaining a clear filtrate.

At a step (210), drying a wet cake of turmeric at 70° C. In an embodiment, the wet cake is dried at 70° C. to obtain the dried turmeric powder.

At step (212), analyzing the oxalic acid content in the dried turmeric powder. In an embodiment, the analysis of oxalic acid content is carried out using, but is not limited to, High Performance Liquid Chromatography (HPLC) or Gas chromatography-mass spectrometry (GC-MS) techniques.

At step (214), analyzing for Microbiological contaminations. In an embodiment, the microbiological contaminations in the dried turmeric powder are analyzed using standard United States Pharmacopeia protocol.

At a step (216), milling, sifting and packaging of the purified turmeric. In an embodiment, the final product is then undergoing in the milling process in order to prepare uniform particle sized turmeric powder. The final turmeric powder is then shifted to the packaging unit for final packing of pure turmeric powder.

The present invention is further described in light of the following experiments which are set forth for an illustration purpose only and not to be construed for limiting the scope of the invention. The following experiments can be scaled up to industrial/commercial scale and the results obtained can be extrapolated to industrial scale.

Example 1

Treatment of Turmeric with Distilled Water

One kilogram (kg) of turmeric powder is extracted with 8 liters of distilled water with the continuous stirring for 2-3 hours. The resultant mixture is then filtered to get the turmeric paste. The paste is again treated multiple times with 3 liters of distilled water to provide a final turmeric paste. The turmeric paste is then dried at room temperature for overnight in order to obtain the final turmeric powder containing less than 2% of the moisture content.

The final turmeric powder is then analyzed for the total content of oxalic acid using the HPLC or GC/MS technique. Lower level of detection (LOD) of the analytical method is 0.01% (100 ppm).

Result: Table 1 illustrates result values after treatment of turmeric with distilled water

TABLE 1

| Treatment of turmeric with distilled water | |
| --- | --- |
| Product for analysis | Total content of oxalic acid (ppm) |
| Turmeric powder after water treatment | 3000 ppm |
| Untreated turmeric powder | 5000 ppm-6000 ppm |

Example 2

Treatment of Turmeric with 1 Normal (N) Inorganic Acid

One kilogram (kg) of turmeric powder is extracted with 8 liters of 0.1 N hydrochloric acid (HCl) with the continuous stirring for 2-3 hours at 40° C. to 50° C. The resultant mixture is then filtered to obtain the turmeric paste. The paste is stirred with 3 liters of distilled water 3 times for 2-3 hours. In order to remove the residual Hydrochloric acid, this method provides the turmeric paste which is then used to produce the dry turmeric powder. The turmeric paste is then dried at room temperature for overnight in order to obtain the final turmeric powder containing less than 2% of the moisture content.

The final dried powder is then analyzed for the total content of oxalic acid using the HPLC or GC/MS technique.

Table 2 illustrates the result values after treatment of turmeric with 1N HCl

TABLE 2

| Treatment of turmeric with 1 Normal (N) inorganic acid | |
| --- | --- |
| Product for analysis | Total content of oxalic acid (ppm) |
| Turmeric powder after inorganic acid treatment | 100 ppm-500 ppm |
| Untreated turmeric powder | 5000 ppm-6000 ppm |

Example 3

Repeated Treatment of Turmeric with 1 Normal Inorganic Acid

One kilogram (kg) of turmeric powder is extracted with 8 liters of 1N hydrochloric acid (HCl) with the continuous stirring for 3 hours at 40° C. to 50° C. The resultant first mixture is then filtered and the filtrate is discarded to obtain a turmeric paste. The paste is again stirred with 4 liters of 1 N HCl for 3 hours, and filtered to obtain the second mixture. This step is again repeated for one more time to get the final turmeric paste. The paste is then stirred for 2 hours-3 hours with 4 liters of distilled water. The step is repeated for multiple times to remove the residual Hydrochloric acid. This process provides the turmeric paste which is then used to produce the dry turmeric powder. The paste is then dried at room temperature for overnight in order to obtain the final turmeric powder containing less than 2% of the moisture content.

The final product is analyzed for the total content of oxalic acid using the HPLC or GC/MS technique.

Table 3 illustrates the result values after repeated treatment of turmeric with 1N HCl.

TABLE 3

| Repeated treatment of turmeric with 1N HCl | |
| --- | --- |
| Product for analysis | Total content of oxalic acid (ppm) |
| Turmeric powder after repeated inorganic acid treatment | <100 ppm |
| Untreated turmeric powder | 5000 ppm-6000 ppm |

Example 4

Repeated Treatment of Turmeric with Distilled Water 2 Normal Inorganic Acid

One kilogram (kg) of turmeric powder is extracted with 8 liters of 2N hydrochloric acid (HCl) with the continuous stirring for 3 hours at 40° C. to 50° C. The resultant first mixture is then filtered and the filtrate is discarded to obtain the turmeric paste. The paste is again stirred with 4 liters of 2 N HCl for 3 hours, and filtered to obtain the second mixture. This step is again repeated for one more time to get the final turmeric paste. The paste is then stirred for 2 hours-3 hours with 4 liters of distilled water. The step is repeated for multiple times to remove the residual Hydrochloric acid. This process provides the turmeric paste, which is then used to produce the dry turmeric powder. The turmeric paste is then dried at room temperature for overnight in order to obtain the final turmeric powder containing less than 2% of the moisture content.

The final product is analyzed for the total content of oxalic acid using the HPLC or GC/MS technique.

Table 4 illustrates result values for repeated treatment of turmeric 2 Normal (N) inorganic acid.

TABLE 4

| Repeated treatment of turmeric 2 Normal (N) inorganic acid. | |
| --- | --- |
| Product for analysis | Total content of oxalic acid (ppm) |
| Turmeric powder after repeated inorganic acid (2N) treatment | <100 ppm |
| Untreated turmeric powder | 5000 ppm-6000 ppm |

As illustrated in table 4, the total content of oxalic acid after repeated treatment with 2 N inorganic acid is <100 ppm, however it has also been observed that the active ingredient, such as curcuminoid tends to degrade when the concentration of inorganic acid is more than 1N HCl concentration.

Table 5 as illustrates below depict the comparison for result of analysis of the oxalic content in turmeric powder before any treatment and after treatment with distilled water, single treatment of inorganic acid, repeated treatment of inorganic acid.

TABLE 5

| Comparison table for total oxalic acid content in turmeric powder after treatment: | |
| --- | --- |
| Product for analysis | Total content of oxalic acid (ppm) |
| Untreated turmeric powder | 5000 ppm-6000 ppm |
| Turmeric powder after water treatment | 3000 ppm |
| Turmeric powder after inorganic acid 1N treatment | 100 ppm-500 ppm |

TABLE 5-continued

| Comparison table for total oxalic acid content in turmeric powder after treatment: | |
| --- | --- |
| Product for analysis | Total content of oxalic acid (ppm) |
| Turmeric powder after repeated inorganic acid (1N) treatment | <100 ppm |

It should be noted that the description merely illustrates the principles of the present invention. It will thus be appreciated that those skilled in the art will be able to devise various arrangements that, although not explicitly described herein, embody the principles of the present invention. Furthermore, all examples recited herein are principally intended expressly to be only for explanatory purposes to help the reader in understanding the principles of the invention and the concepts contributed by the inventor to furthering the art, and are to be construed as being without limitation to such specifically recited examples and conditions. Moreover, all statements herein reciting principles, aspects, and embodiments of the invention, as well as specific examples thereof, are intended to encompass equivalents thereof.

I claim:

1. A method for removing oxalic acid from turmeric spice, the method comprising:
   (a) preparing a turmeric powder from a turmeric rhizome;
   (b) extracting the turmeric powder with an inorganic acid of 1 Normal (N) concentration, wherein the extraction comprises stirring the turmeric powder in 8 liters of the inorganic acid for 3 hours with constant agitation at 40° C. to 50° C. to obtain a first stirred solution;
   (c) filtering the first stirred solution to obtain a first turmeric paste;
   (d) extracting the first turmeric paste with the inorganic acid of 1 Normal (N) concentration, wherein the extraction comprises stirring the turmeric paste in 4 liters of the inorganic acid for 3 hours with constant agitation at 40° C. to 50° C. to obtain a second stirred solution;
   (e) filtering the second stirred solution to obtain a second turmeric paste;
   (f) washing the second turmeric paste with a distilled water to obtain a washed turmeric paste, whereby residual chloride content is removed;
   (g) drying the washed turmeric paste at room temperature and measuring a moisture content of the dried turmeric powder to obtain a dried turmeric powder with a moisture content below 2%; and
   (h) analyzing a content of the oxalic acid content of the dried turmeric powder;
      wherein the content of the oxalic acid is gradually reduced after each of steps (b) and (d);
      wherein a total content of the oxalic acid is below 100 ppm; and
      wherein the curcuminoids in the dried turmeric powder are not degraded.

2. The method according to claim 1, wherein in step (a) the turmeric powder is obtained by grinding the rhizome to make a powder and passed 100% through #100 mesh.

3. The method according to claim 1, wherein the temperature of the distilled water is between room temperature and 50° C.

4. The method according to claim 1, wherein the inorganic acid is selected from a group consisting of hydrochloric acid (HCl) and sulfuric acid ($H_2SO_4$).

5. The method according to claim 1, wherein the inorganic acid is hydrochloric acid (HCl).

6. The method according to claim 1, wherein a ratio of the turmeric powder to the inorganic acid is between 1:8 and 1:4.

7. The method according to claim 1, wherein in step (h) analyzing the content of the oxalic acid is carried out using a chromatography technique.

8. The method according to claim 1, wherein in step (f) washing the second turmeric paste with the distilled water for removing the residual chloride content is repeated until a clear filtrate is obtained.

* * * * *